US009895197B2

(12) United States Patent
Poquet et al.

(10) Patent No.: US 9,895,197 B2
(45) Date of Patent: Feb. 20, 2018

(54) DEVICE FOR GUIDING A MEDICAL INSTRUMENT INSERTED INTO A NATURAL DUCT OR AN ARTIFICIAL DUCT OF A PATIENT

(71) Applicants: Cecile Poquet, Ivry-sur-seine (FR); Pierre Mozer, Vincennes (FR); Michael Baumann, Grenoble (FR); Marie-Aude Vitrani, Paris (FR); Guillaume Morel, Paris (FR); Antoine Leroy, Meylan (FR); Patrick Henri, Bois-Colombes (FR)

(72) Inventors: Cecile Poquet, Ivry-sur-seine (FR); Pierre Mozer, Vincennes (FR); Michael Baumann, Grenoble (FR); Marie-Aude Vitrani, Paris (FR); Guillaume Morel, Paris (FR); Antoine Leroy, Meylan (FR); Patrick Henri, Bois-Colombes (FR)

(73) Assignees: UNIVERSITE PIERRE ET MARIE CURIE (PARIS 6), Paris (FR); CENTRE NATIONAL DE LA RECHERCHE SCIENTIFIQUE, Paris (FR); KIELIS, Grenoble (FR)

( * ) Notice: Subject to any disclaimer, the term of this patent is extended or adjusted under 35 U.S.C. 154(b) by 515 days.

(21) Appl. No.: 14/348,323

(22) PCT Filed: Sep. 28, 2012

(86) PCT No.: PCT/EP2012/069236
§ 371 (c)(1),
(2) Date: Mar. 28, 2014

(87) PCT Pub. No.: WO2013/045645
PCT Pub. Date: Apr. 4, 2013

(65) Prior Publication Data
US 2014/0296876 A1 Oct. 2, 2014

(30) Foreign Application Priority Data

Sep. 30, 2011 (FR) ..................... 11 58880

(51) Int. Cl.
*A61B 34/00* (2016.01)
*A61B 19/00* (2006.01)
(Continued)

(52) U.S. Cl.
CPC .............. *A61B 19/26* (2013.01); *A61B 34/74* (2016.02); *A61B 90/50* (2016.02);
(Continued)

(58) Field of Classification Search
CPC .............. A61B 90/50; A61B 2090/508; A61B 2034/2065; A61M 2025/0166
See application file for complete search history.

(56) References Cited

U.S. PATENT DOCUMENTS 5,078,140 A * 1/1992 Kwoh ................... A61B 19/22
378/20
2002/0177857 A1 11/2002 Otsuka et al.
(Continued)

FOREIGN PATENT DOCUMENTS

DE 10 2006 007 858 A1 8/2007
EP 1 520 548 A2 4/2005
WO 2011/058530 A1 5/2011

*Primary Examiner* — Thomas McEvoy
(74) *Attorney, Agent, or Firm* — Sughrue Mion, PLLC

(57) ABSTRACT

A device for guiding a medical instrument (2) inserted into a natural duct (101) or an artificial duct of a patient in order to bring at least a distal end (1) of the instrument in proximity to an internal organ (100). The device includes an articulated arm (3) with a plurality of degrees of freedom, for moving a proximal end (4) of the instrument, and a controlled blocking mechanism (7) for blocking the degrees of freedom of the articulated arm. The blocking mechanism is designed in such a way that, for at least one of the degrees (Continued)

of freedom, a blockage imposed on the degree of freedom can be released when an outer stress exerted on the instrument (2) exceeds a predetermined threshold.

23 Claims, 5 Drawing Sheets

(51) Int. Cl.
*A61B 90/50* (2016.01)
*A61B 10/02* (2006.01)
*A61B 17/00* (2006.01)
*A61B 18/00* (2006.01)
*A61B 90/00* (2016.01)
*A61B 34/20* (2016.01)

(52) U.S. Cl.
CPC . *A61B 10/0241* (2013.01); *A61B 2017/00199* (2013.01); *A61B 2017/00203* (2013.01); *A61B 2017/00274* (2013.01); *A61B 2017/00398* (2013.01); *A61B 2017/00694* (2013.01); *A61B 2018/00547* (2013.01); *A61B 2034/2065* (2016.02); *A61B 2090/065* (2016.02); *A61B 2090/0808* (2016.02); *A61B 2090/08021* (2016.02); *A61B 2090/508* (2016.02)

(56) References Cited

U.S. PATENT DOCUMENTS

| | | |
|---|---|---|
| 2004/0092810 A1 | 5/2004 | Daum et al. |
| 2008/0065109 A1* | 3/2008 | Larkin ............... A61B 1/00087 606/130 |
| 2009/0000627 A1 | 1/2009 | Quaid et al. |
| 2012/0283747 A1* | 11/2012 | Popovic ........................ 606/130 |

* cited by examiner

DEVICE FOR GUIDING A MEDICAL INSTRUMENT INSERTED INTO A NATURAL DUCT OR AN ARTIFICIAL DUCT OF A PATIENT

The invention relates to a device for guiding a medical instrument inserted into a natural or artificial duct of a patient in order to bring at least a distal end of the instrument in proximity to an internal organ.

TECHNOLOGICAL BACKGROUND TO THE INVENTION

"Open" surgery is known to be very demanding for patients. For this reason, practitioners are increasingly using mini-invasive operations in which medical instruments are inserted into a natural duct of the patient (vagina, rectum, auditory meatus etc.) or into an artificial duct connected to the body of the patient (cannula, artificial vein, trocar etc.).

In urology, it is known that a prostate biopsy can be carried out to screen for possible prostate cancer. This involves taking tissue samples from within the prostate, said samples then being analyzed in a laboratory, to detect the presence of any cancer cells. For this, the patient lies on his side. An instrument comprising an ultrasound sensor and a needle guide with a biopsy needle is then inserted into the natural duct formed by the rectum. Using this instrument, the surgeon perforates the colon wall to access the prostate and thus take tissue samples.

To perform the biopsy the only images the surgeon can use are two-dimensional ones taken in real time by the ultrasound sensor. The surgeon therefore has to imagine a three-dimensional representation of the prostate in order to take the samples, in the knowledge that the prostate tends to be displaced or deformed by the movements of the instrument.

It therefore proves extremely difficult for a surgeon to know the exact locations from which the needle will take samples of prostate tissue. However, aspirations from the prostate should be done uniformly over the whole prostate, since cancer cells cannot be detected directly by the sensor.

Devices have recently been developed to help the surgeon perform the various types of aspiration very precisely. These new devices comprise sensors that can provide three-dimensional images of the prostate. The operating principle of said sensors is to plan the theoretical positions for the aspirations and to study the deformation of the prostate during the biopsy. The theoretical aspiration plan is then amended depending on the study of deformation of the prostate so that the aspirations can be done in the right places.

However, the sensors have to scan the prostate in order to provide three-dimensional images and thus produce images not in real time but with a few seconds' delay. Any movement of the sensor while it is scanning the prostate should therefore be limited as far as possible. Similarly, any unnecessary movement of the instrument when the biopsy needle is inserted into the prostate should be limited as far as possible, so that the aspiration can be done in the right place.

It is possible that the patient is not under local anesthesia and/or is not immobilized. This means that the patient—and thus all the tissues of the natural or artificial duct with which the instrument can come into contact—can move during the operation. Furthermore, it proves difficult for a surgeon to hold the instrument still in a given position to allow the sensor to scan the prostate and to carry out aspirations in the desired places.

To assist the surgeon, there are known devices for guiding an instrument comprising an articulated arm for moving a proximal end of the instrument. The surgeon can then control the articulated arm so that it locks the instrument in a given position. This makes it easy for the surgeon to perform an operation on the patient, such as taking a tissue sample or acquiring images via the sensor.

However, the instrument—locked in a given position like this—opposes any movements of the patient, which can be uncomfortable for the patient and even damage some tissues.

Thus there are known devices for guiding an instrument comprising an articulated arm for moving a proximal end of the instrument, the articulated arm being linked to the proximal end by a gimbal or ball-joint type link.

This means that, even if the surgeon controls the articulated arm so that it locks the instrument in a given position, the ball coupling or gimbal nevertheless allows the patient to move. But each time the patient moves, the instrument is then displaced and the surgeon has to reposition the instrument correctly.

Document WO 2011/058530 discloses a medical instrument guide comprising an articulated arm that can lock the medical instrument in a given position. The articulated arm is controlled so that when the effort exerted by the surgeon on the instrument exceeds a predetermined threshold of effort, locking of the articulated arm is released. However, the effort exerted is measured by effort sensors.

SUBJECT-MATTER OF THE INVENTION

An aim of the invention is to propose a device for guiding a medical instrument inserted into a natural or artificial duct of a patient that is more advanced than existing devices.

BRIEF DESCRIPTION OF THE INVENTION

With a view to achieving this aim, a device is proposed for guiding a medical instrument inserted into a natural or artificial duct of a patient in order to bring at least a distal end of the instrument in proximity to an internal organ, the device comprising an articulated arm with a plurality of degrees of freedom, for moving a proximal end of the instrument, controlled locking means for restricting the degrees of freedom of the articulated arm, the locking means being designed so that, for at least one of the degrees of freedom, imposed restriction of said degree of freedom can be released when an external effort exerted on the instrument exceeds a predetermined threshold, and a computing module for controlling the locking means.

According to the invention the device comprises image acquisition means, carried by the instrument, for acquiring images of the organ, the computing module being based at least on said images in order to control the locking means.

In this way, the instrument is immobilized in a given position, to make it easy for the surgeon to perform an operation on the patient (scan of the organ, biopsy of the organ etc.) but locking can be released such that, if the external effort comes from a sudden movement of the patient, the anatomy of the patient is well protected. On the other hand, small movements by the patient do not disturb the work of the surgeon.

Because the locking means are controlled on the basis of the images of the organ, the articulated arm can be unlocked not only when the external effort results from the movement of a surgeon acting on the organ of the patient but also when the external effort is the result of patient movement, for example if the latter sneezes. This gives better protection to the anatomy of the patient.

The phrase "release locking" means here that when an external effort exceeds a predetermined threshold, the locking means are designed to make the articulated arm mobile again, in the degree of freedom that was initially restricted, and the instrument can then move in response to the external effort being exerted on it.

Preferably, the computing module comprises means for storing a position to be reached by the instrument relative to the organ, the computing module controlling the locking means, on the basis of the images taken by the image acquisition means, so as to impose restriction on at least one of the degrees of freedom of the articulated arm when the instrument is substantially close to said position.

This monitoring allows the articulated arm to be locked in a precise desired position, which facilitates the work of the surgeon.

BRIEF DESCRIPTION OF THE DRAWINGS

It will be easier to understand the invention in the light of the following description of non-restrictive embodiments of the invention with reference to the attached figures, in which.

DETAILED DESCRIPTION OF THE INVENTION

Figure 1:
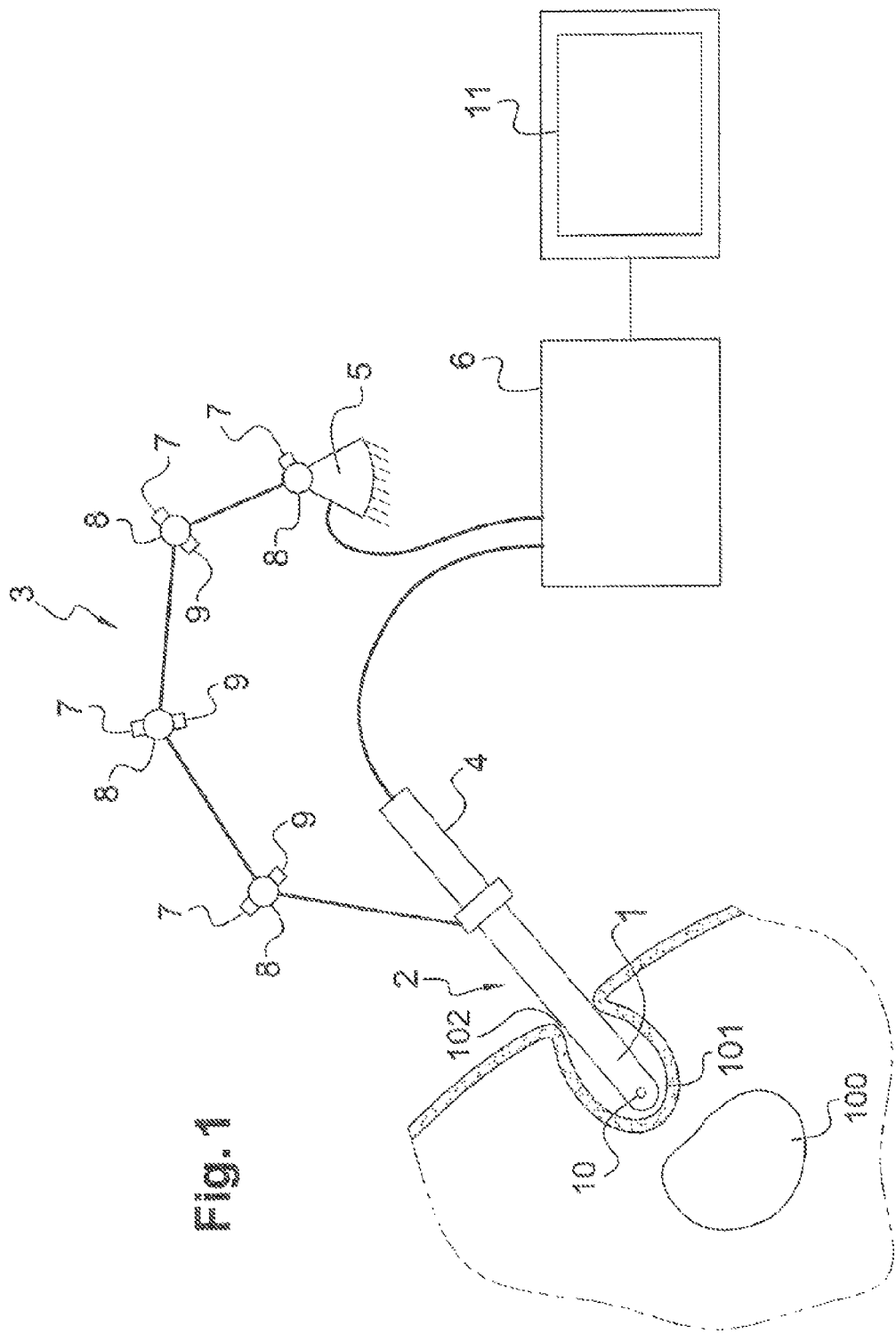
FIG. 1 is a diagrammatic view of a guiding device according to the invention, part of said guiding device being shown inserted into a duct of the patient.

With reference to FIG. 1, the guiding device according to the invention is intended to bring at least a distal end 1 of a medical instrument 2 in proximity to an internal organ 100 of a patient. The medical instrument 2 is for example an ultrasound sensor, a needle guide etc. The medical instrument 2 is inserted into a duct 101 of the patient, which can be natural (rectum, vagina, auditory meatus etc.) or artificial (cannula, trocar, artificial vein etc.), via an orifice 102 of the patient, which can be natural (anus etc.) or artificial (incision etc.).

The guiding device comprises an articulated arm 3 with a plurality of degrees of freedom, for moving a proximal end 4 of the instrument. The proximal end means, of course, the end opposite the one inserted into the body of the patient. The articulated arm 3 is here connected at one of its ends to a base 5 and, at the other end, carries the medical instrument 2.

The guiding device further comprises controlled means for restricting the degree of freedom of the articulated arm 3 in order to lock the articulated arm 3 in a given position. The locking means thus make it easier to position the medical instrument 2 and hold it in a particular position. The locking means comprise, for example, at least one motor mounted on an articulation of the articulated arm 3, at least one braking member arranged on an articulation of the articulated arm 3 such as an electromagnetic brake, a friction brake etc., and at least one gear clutch or dog clutch mounted on an articulation of the articulated arm 3 etc.

The locking means are designed so that, for at least one of the degrees of freedom of the articulated arm 3, imposed restriction of said degree of freedom can be released when an external effort exerted on the medical instrument 2 exceeds a predetermined threshold. The external effort is, for example, a movement by the patient or a movement by a surgeon working on the organ of the patient. The articulated arm can then be moved again in the unrestricted degree of freedom so that the instrument can be moved in response to the external effort being exerted on it. Advantageously, movement imposed on the instrument by the external effort is permitted but is still braked by the locking means. According to a preferred embodiment, the locking means are designed so that the greater the external effort, the less the locking means brake the movement imposed on the instrument by the external effort. Preferably, the guiding device is designed so that when locking is released, no action can be performed on the organ 100 by the instrument 2.

The locking means are, for example, designed so that the predetermined threshold is defined directly by the surgeon before the start of or during an investigation. According to a variant, the locking means are designed so that the predetermined threshold is determined according to external efforts already exerted on the instrument 2 when the locking means impose restriction on the degrees of freedom of the articulated arm 3. Thus, if the instrument 2 is locked in a position for which external efforts are already being exerted on the instrument 2, locking will not be released at the small additional external effort, the predetermined threshold being defined relative to the external efforts initially exerted on the instrument 2.

According to the invention, the locking means are controlled by a computing member 6 of the guiding device, also known as a computing module 6 of the control device. For example, when the locking means comprise at least one motor mounted on an articulation of the articulated arm 3, the computing module 6 modulates an electric current passing through the motor in order to electronically release the locking of the locking means.

According to the invention, the device comprises means 10, carried by the medical instrument 2, for acquiring images of the organ 100. The medical instrument 2 thus comprises the means 10 for acquiring images of the organ 100 and is linked to said image acquisition means 10. The images taken by said image acquisition means are thus representative of the position of said means with respect to the organ 100 in the coordinate system of the guiding device.

According to the invention, the computing module 6 is based on the images taken by the image acquisition means 10 for controlling the locking means. According to a preferred embodiment, the computing module 6 comprises means for estimating the displacement of the organ 100 relative to the instrument 2 and/or any deformation of the organ 100, on the basis of images supplied by the image acquisition means 10 when the instrument 2 is in contact with the organ. The computing module 6 further comprises monitoring means communicating with the estimating means so as to determine on the basis of the estimated displacement and/or deformation whether locking should be released.

Figure 3:
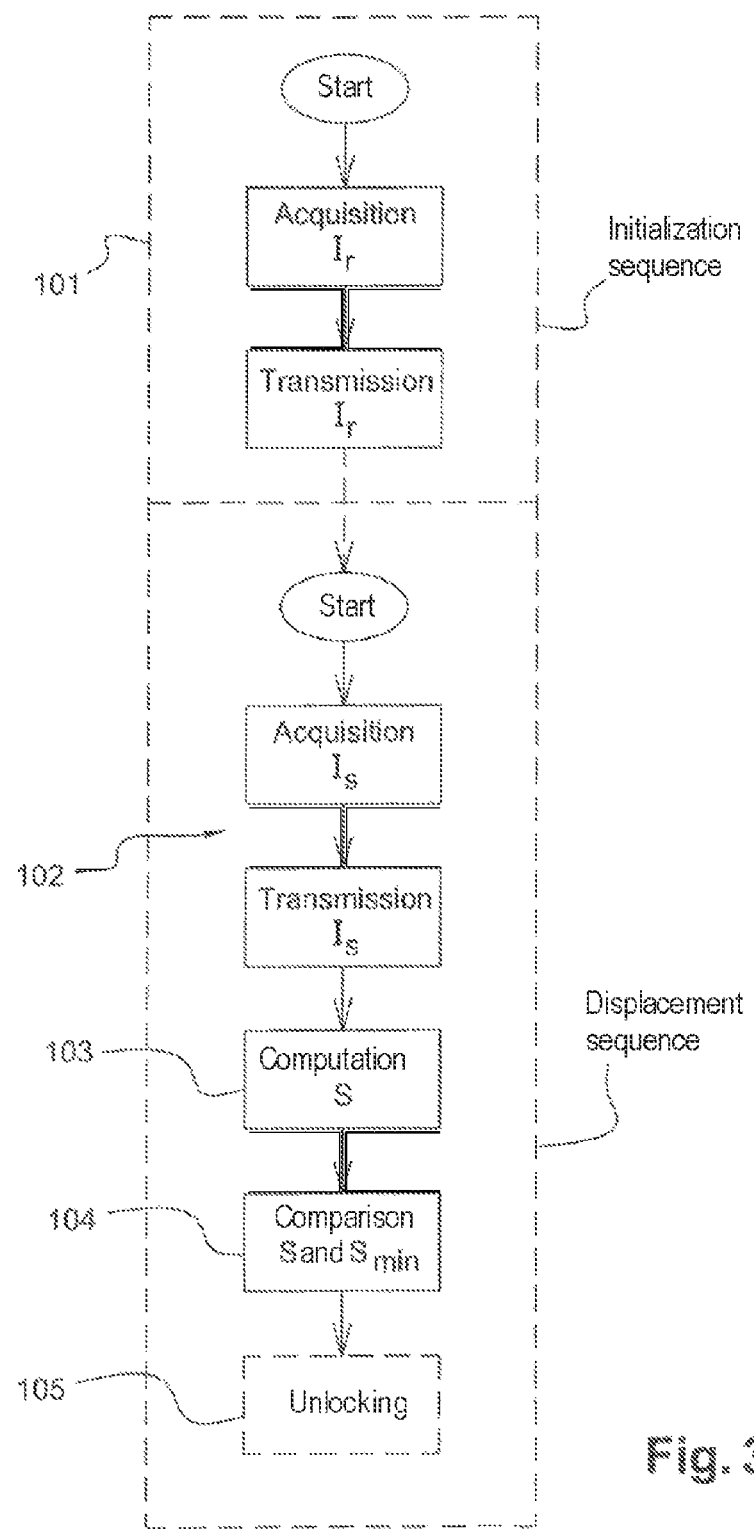
FIG. 3 is a diagram illustrating the various steps in a first embodiment of the device illustrated in FIG. 1.

With reference to FIG. 3, in a first embodiment the computing module 6 controls the unlocking of the locking means as follows.

In an initialization sequence, during a first step 101, the acquisition means 10 acquire a first image known as the reference image $I_r$. Said reference image is then sent to the computing module 6. The reference image is for example a general image of the organ 100 or an image of a particular area of the organ 100. The reference image is, for example, two-dimensional or three-dimensional. As a variant, the reference image is not acquired by the acquisition means 10 but rather by means of other medical investigations (such as Magnetic Resonance Imaging) and supplied to the computing module 6.

In a sequence of moving the instrument 2, during a second step 102, the acquisition means 10 acquire at least one image $I_s$ and send it to the computing module 6.

In a third step 103, the estimating means evaluate a similarity parameter S between the reference image $I_r$ and the image $I_s$. This evaluation is, for example, made using the formula:

$$S = Sim(I_s, I_r \circ T_m)$$

where Sim is a function of measurement of the cross-correlation of two images (or two subsets of images) that is determined on the gray scale of the images (or elements of the two subsets of images).

In a fourth step 104, the estimating means compare the similarity parameter S with a predetermined similarity threshold $S_{min}$ that is representative of the predetermined effort threshold of the locking means. Said similarity threshold $S_{min}$ is for example computed by statistical analysis of data from several initial tests such as a Bayesian inference algorithm.

In a fifth step 105, the monitoring means control the locking means to release imposed locking if the similarity parameter S is below the predetermined similarity threshold $S_{min}$.

If the organ 100 is displaced or deformed between the reference image $I_r$ and the image $I_s$, this means that the instrument 2 has been moved relative to the organ 100 and might be in contact with the organ 100, the displacement of the instrument 2 being due to an external effort caused by a movement by the patient or a movement by the surgeon. The computing module 6 thus estimates the external efforts exerted on the instrument 2 on the basis of the images acquired by the acquisition means 10, by calculating the movements of the instrument 2 relative to the organ 100.

Figure 4:
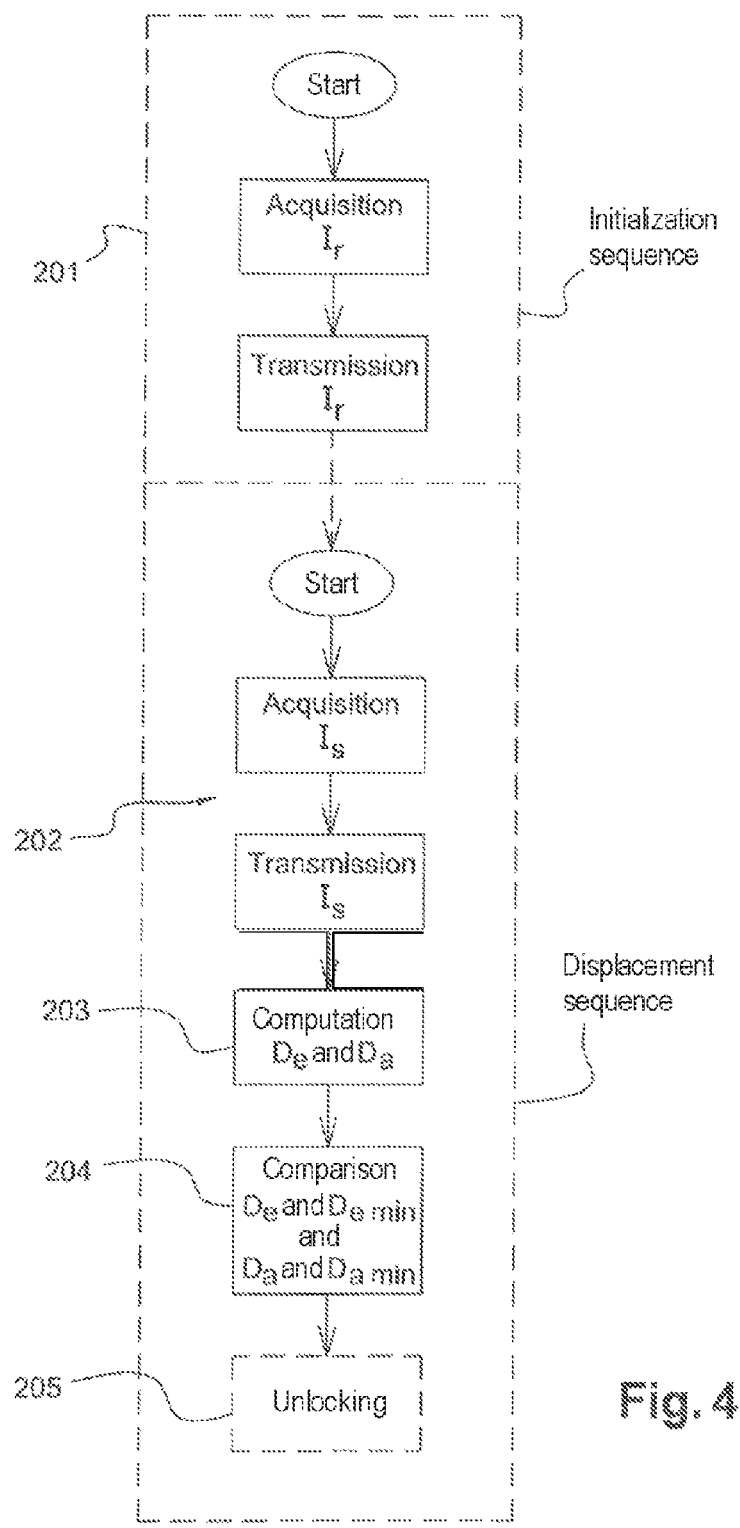
FIG. 4 is a diagram illustrating the various steps in a second embodiment of the device illustrated in FIG. 1.

With reference to FIG. 4, in a second embodiment the computing module 6 controls the unlocking of the locking means as follows.

In an initialization sequence, during a first step 201, the acquisition means 10 acquire a first image known as the reference image $I_r$. Said reference image is then sent to the computing module 6. As a variant, the reference image $I_r$ is not acquired by the acquisition means 10 but rather by means of other medical investigations and supplied to the computing module 6. In all cases, it is preferable but not restrictive in this embodiment for the reference image $I_r$ to be a general, three-dimensional image of the organ 100.

In a sequence of moving the instrument 2, during a second step 202, the acquisition means 10 acquire at least one image $I_s$ and send it to the computing module 6.

In a third step 203, the estimating means evaluate a Euclidean distance parameter $D_e$ between the reference image $I_r$ and the image $I_s$ and an angular distance parameter $D_a$ between the reference image $I_4$ and the image $I_s$. This evaluation is for example performed by realigning the two images or by searching for a function to minimize a similarity parameter between the two images using optimization by the Powell-Brent method.

In a fourth step 204, the estimating means compare the Euclidean distance parameter $D_e$ with a predetermined Euclidean distance threshold $De_{min}$ that is representative of the predetermined effort threshold of the locking means. The estimating means further compare the angular distance parameter $D_a$ with a predetermined angular distance threshold $Da_{min}$ that is representative of the predetermined effort threshold of the locking means. Said thresholds $De_{min}$ and $Da_{min}$ are for example computed on the basis of an acceptable margin of error between the desired position of the instrument 2 and the actual position of the instrument 2.

In a fifth step 205, the monitoring means control the locking means to release imposed locking if the Euclidean distance parameter $D_e$. exceeds the predetermined Euclidean distance threshold $De_{min}$ or if the angular distance parameter $D_a$ exceeds the predetermined angular distance threshold $Da_{min}$.

Figure 5:
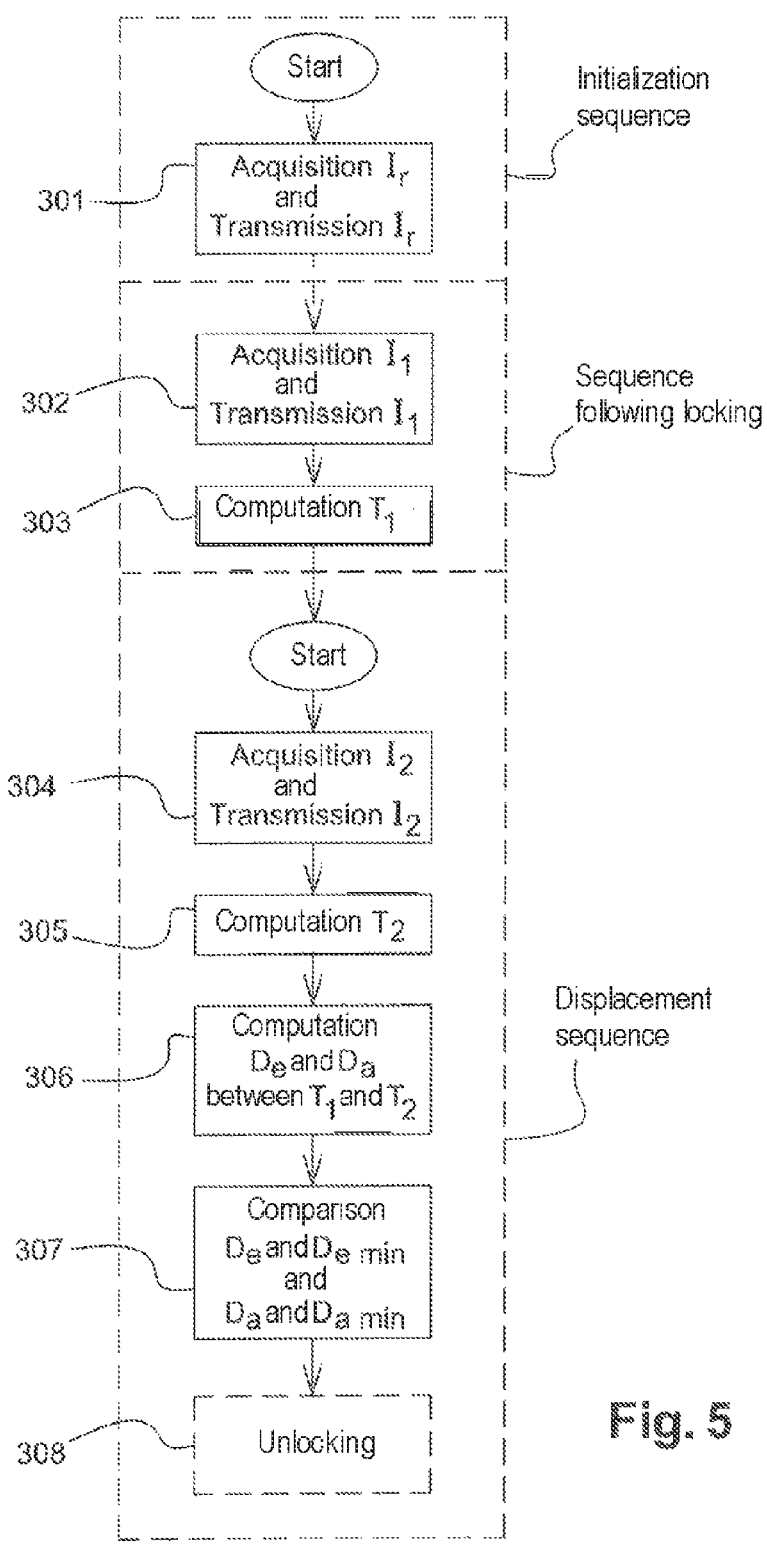
FIG. 5 is a diagram illustrating the various steps in a third embodiment of the device illustrated in FIG. 1.

With reference to FIG. 5, in a third embodiment the computing module 6 controls the unlocking of the locking means as follows.

In an initialization sequence, during a first step 301, the acquisition means 10 acquire a first image known as the reference image $I_r$. Said reference image is then sent to the computing module 6.

Following locking of the locking means, during a second step 302, the acquisition means 10 acquire at least a first image $I_1$ and send it to the computing module 6.

In a third step 303, the estimating means evaluate a first position $T_1$ of the first image $I_1$ relative to the reference image $I_r$.

In a sequence of moving the instrument 2, during a fourth step 304, the acquisition means 10 acquire at least a second image $I_2$ and send it to the computing module 6.

In a fifth step 305, the estimating means evaluate a second position $T_2$ of the second image $I_2$ relative to the reference image $I_r$.

In a sixth step 306, the estimating means evaluate a Euclidean distance parameter $D_e$ between the first position $T_1$ and the second position $T_2$ and an angular distance parameter $D_a$ between the first position $T_1$ and the second position $T_2$.

In a seventh step 307, the estimating means compare the Euclidean distance parameter $D_e$ with a predetermined Euclidean distance threshold $De_{min}$ that is representative of the predetermined effort threshold of the locking means. The estimating means further compare the angular distance parameter $D_a$ with a predetermined angular distance threshold $Da_{min}$ that is representative of the predetermined effort threshold of the locking means.

In an eighth step 308, the monitoring means control the locking means to enforce imposed locking if the Euclidean distance parameter $D_e$ is below the predetermined Euclidean distance threshold $De_{min}$ or if the angular distance parameter $D_a$ is below the predetermined angular distance threshold $Da_{min}$.

In a specific manner, to control the locking means, the computing module 6 further determines the value of the external effort applied to the instrument 2, using effort sensors. In a variant, a sensor, for example an angular sensor 7, is arranged on each articulation 8 of the articulated arm 3 in order to send to the computing module 6 a signal representative of the relative position of two elements of the articulated arm 3 forming the associated articulation 8. Advantageously, by means of signals from the angular sensors 7, the computing module 6 can estimate the position of the instrument 2 in a coordinate system of the guiding device. This estimate can, for example, be sent to the surgeon to help him visualize the position of the instrument 2 with respect to the organ 100.

In a preferred manner, the guiding device comprises different operating modes. According to a first operating mode of the guiding device, the locking means are deactivated so that no degree of freedom of the articulated arm 3 is locked. The articulated arm 3 can therefore be moved freely, either automatically and/or manually by the surgeon. In a second operating mode, the locking means are activated so that the degrees of freedom of the articulated arm 3 are locked. The proximal end 1 of the instrument 2 is therefore locked in a given position.

In an operation, the surgeon can in this way switch as many times as necessary between the two operating modes of the guiding device. For example, the surgeon can in a first stage select the first operating mode in order to freely position the distal end 1 of the instrument 2 in the natural duct 101 of the patient. Then, in a second stage, the surgeon selects the second operating mode, to keep the instrument in a given position.

Preferably, the guiding device comprises means for selecting the operating modes of the guiding device. The selection means comprise for example one or more switches arranged, for example, on the computing module 6 and/or the articulated arm 3. As a variant, the selection means comprise one or more pedals arranged at the foot of the guiding device, a voice command system etc. Preferably, the selection means are designed so that the surgeon can switch from one operating mode to another instantaneously and at any time during the intervention.

Preferably, and in a manner known per se, the guiding device comprises weight balancers 9 to balance the articulated arm 3 so that the proximal end 4 of the instrument 2 is held in a particular position, preferably in the center of the duct 101. For instance, when changing from the second operating mode to the first operating mode, the instrument 2 remains substantially in the center of the orifice 102.

Preferably, the guiding device comprises means for communication with the surgeon, for example, to indicate the position of the instrument 2 relative to the organ 100 so as to help the surgeon with planning and/or carrying out a surgical procedure, warn that imposed locking has been released, give a value for the external efforts applied to the instrument 2 etc.

Advantageously, when the communication means indicate that imposed locking has been released, the surgeon is warned that the patient may have moved by a large amplitude and he can therefore take account of this before performing a surgical procedure. In the case of aspiration, for example, the surgeon can check that the instrument is indeed correctly positioned with respect to the organ.

The communication means comprise, for example, a display screen 11.

Preferably, the computing module 6 comprises means for storing a position to be reached by the instrument 2 relative to the organ 100. This position to be reached is, for example, entered by the surgeon before the start of the operation or is the position in which the instrument was located before the locking means were released.

When the surgeon moves the instrument 2, the computing module 6 then controls the locking means on the basis of the images taken by the image acquisition means 10 so as to impose restriction on at least one of the degrees of freedom of the articulated arm 3 when the instrument is substantially close to said position.

It is thus possible to lock the arm 3 in a precise desired position, which facilitates the work of the surgeon.

Here, the computing module 6 controls the locking of the locking means in a similar way to how it controls the unlocking of the locking means, as has already been described.

For example, the computing module 6 controls the locking of the locking means using the following command process:
   acquiring at least one reference image of the organ 100,
   acquiring at least a first image of the organ 100,
   computing a similarity parameter between the reference image and the first image,
   comparing the similarity parameter with a predetermined similarity threshold that is representative of the predetermined effort threshold,
   controlling the locking means to lock the articulated arm if the similarity parameter is above the predetermined similarity threshold.

As a variant, the computing module 6 controls the locking of the locking means according to the following command process:
   acquiring at least one reference image of the organ 100,
   acquiring at least a first image of the organ 100,
   computing a Euclidean distance parameter and an angular distance parameter between the reference image and the first image,
   comparing the Euclidean distance parameter with a predetermined Euclidean distance threshold and comparing the angular distance parameter with a predetermined angular distance threshold, each of the thresholds being representative of the predetermined effort threshold,
   controlling the locking means to lock the articulated arm if the Euclidean distance parameter is below the predetermined Euclidean distance threshold or if the angular distance parameter is below the predetermined angular distance threshold.

A particular embodiment will now be described. This embodiment is naturally not restrictive.

Figure 2:
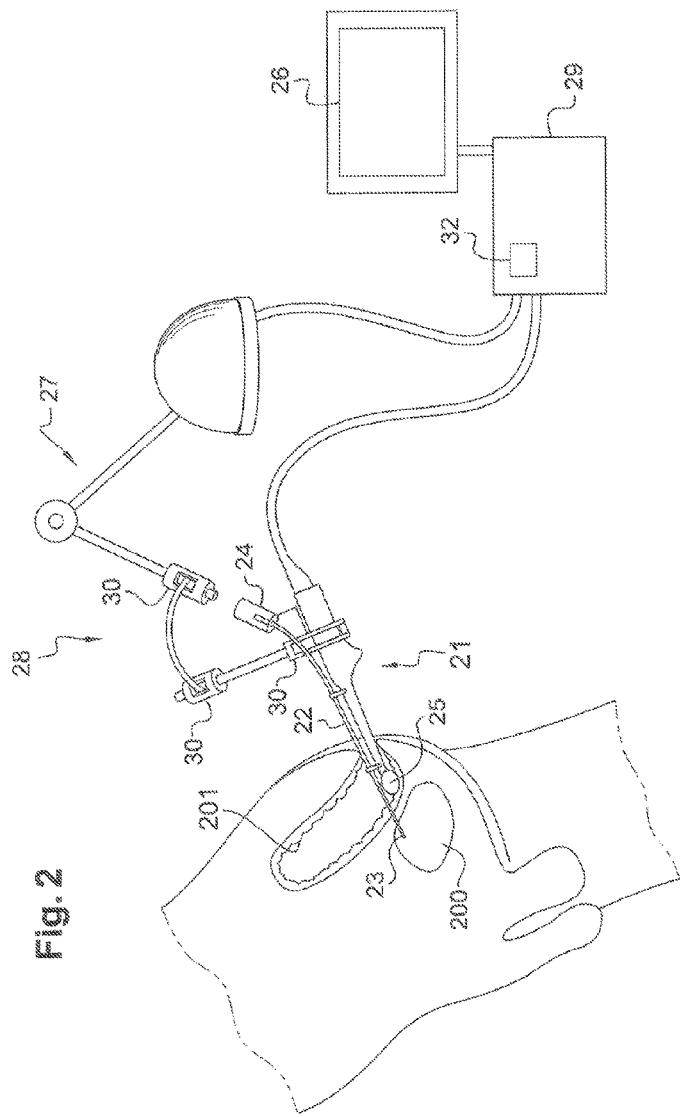
FIG. 2 is a diagrammatic view of a guiding device according to a particular embodiment of the invention, part of said guiding device being shown inserted into the rectum of a patient.

With reference to FIG. 2, the guiding device according to the invention is here intended to bring a medical instrument 21 in proximity to the prostate 200 of a patient. Here, the medical instrument 21 comprises a needle guide 22 carrying a biopsy needle 23, one end of which is intended for carrying out aspiration on the prostate 200. The instrument 21 further comprises means for actuating the needle guide 24 in order to insert and remove the needle 23 from the prostate 200. The instrument 21 also comprises means for acquiring images of the prostate 200 in order to position the biopsy needle 23 relative to the prostate 200. For this purpose, the image acquisition means comprise a sensor 25. Preferably, the sensor 25 is an ultrasound sensor allowing three-dimensional images of the prostate 200 to be acquired.

The guiding device according to the invention comprises an articulated arm 27 with a plurality of degrees of freedom for moving a proximal end of the instrument 21, i.e. to move the sensor 25 and the biopsy needle 23, in the natural duct formed by the rectum 201. Here, the articulated arm 27 is shaped so as to allow the proximal end of the instrument 21 to be moved, by moving the proximal end of the instrument 21 at least once in an axis substantially co-linear with an approach to the rectum 201 when the patient is lying down. The articulated arm 27 is for example a Virtuose 3D robot from the Haption company modified so that the articulated arm 27 is linked to the proximal end of the instrument 21 by a ball-joint type link 28. Naturally, the articulated arm 27 is designed so that the ball coupling 28 cannot influence the operation of the sensor 25 or the biopsy needle 23.

In a preferred manner, the articulated arm 27 is designed so that the ball coupling 28 cannot prevent a surgeon from correctly grasping the proximal end of the instrument 21.

According to the invention, the guiding device further comprises controlled means for restricting the degrees of freedom of the articulated arm 27. Here, the locking means are designed to restrict each degree of freedom of the ball coupling 28 such that locking imposed on the ball coupling 28 can be released when an external effort exerted on the instrument 21 exceeds a predetermined threshold. To this end, the locking means comprise brakes 30, for example friction brakes, arranged in each of the degrees of freedom of the ball coupling 28. Preferably, the guiding device is designed so that when locking is released, no action can be performed on the prostate 200 by the biopsy needle 23.

The guiding device comprises a computing module 29 to control said articulated arm 27.

The computing module 29 communicates with the sensor 25 in order to receive and analyze data transmitted by the sensor 25. Images taken by the sensor 25 are representative of the position of the sensor 25 with respect to the prostate 200 in the coordinate system of the guiding device. Since the sensor 25 is at a distance from and in an orientation fixed relative to the biopsy needle 23 when the biopsy needle 23 is in the retracted position, these images are also representative of a position of the biopsy needle 23 with respect to the prostate 200.

It is therefore possible to correlate the coordinate system of the guiding device with the images taken by the sensor 25. The computing module 29 can thus superimpose, over an image of the prostate 200 taken by the sensor 25, an aspiration target defined beforehand in the coordinate system of the guiding device. The computing module 29 can also superimpose a current trajectory of the biopsy needle 23 deduced from the images taken by the sensor 25 over an image linked to the coordinate system of the guiding device, illustrating previous aspiration trajectories.

To control the locking means, the computing module 29 estimates the external efforts exerted on the instrument 21, on the basis of images taken by the sensor 25 so as to control, here, unlocking of the locking means and also locking of the locking means.

Here, the guiding device further comprises sensors arranged on the various articulations of the articulated arm 27 so that, using the signals from the sensors, the computing module 29 can estimate the position of the instrument 21 in a coordinate system of the guiding device.

The guiding device in this case comprises a display screen 26 for the images taken by the sensor 25 to give the surgeon visual feedback so he can estimate the position of the biopsy needle 23 relative to the prostate 200.

In a preferred manner, the guiding device comprises different operating modes. According to a first operating mode of the guiding device, no degree of freedom of the articulated arm 27 is restricted. The articulated arm 27 can be moved freely, either automatically and/or manually by the surgeon. In a second operating mode, the degrees of freedom of the articulated arm 27 are restricted. The guiding device further comprises means 32 for selecting the operating modes of the guiding device.

Here, the computing module 29 also monitors the locking means of the articulated arm 27 and, in particular, brakes 30, so that it permits or prohibits the restriction of the degrees of freedom of the articulated arm 27 depending on the operating mode of the guiding device selected.

At present, image acquisition using the sensor 25 and analysis of these images by the computing module 29 cannot be carried out in real time. By using the guiding device according to the invention, it is possible to hold the instrument 2 in a fixed position long enough for the sensor 25 to acquire images of the prostate 200 without said images being deformed by movement of the instrument 21 and long enough for the computing module 29 to analyze these images in order to deduce from them the position of the biopsy needle with respect to the prostate 200. In this way, the surgeon can be sure that the biopsy needle is correctly positioned. Furthermore, it requires a lot of dexterity on the part of the surgeon to insert a biopsy needle into the prostate 200 without moving the instrument. By using the guiding device according to the invention, the instrument 2 can be held in a fixed position throughout the aspiration. These various characteristics of the device make sure that the needle 22 is inserted in the desired place in the prostate 200, while respecting the anatomy of the patient. Moreover, the guiding device according to the invention facilitates the work of the surgeon, who no longer has to hold the instrument immobile throughout the aspiration.

Naturally, the invention is not limited to the embodiment described, and variant embodiments can be implemented without leaving the context of the invention as defined by the claims.

The invention claimed is:

1. A device for guiding a medical instrument (2; 21) inserted into a natural duct (101; 201) or an artificial duct of a patient in order to bring at least a distal end (1) of the instrument in proximity to an internal organ (100; 200), the device comprising:
    an articulated arm (3; 27) with a plurality of degrees of freedom for moving a proximal end (4) of the instrument,
    controlled locking means (7; 30) for restricting the degrees of freedom of the articulated arm, the locking means being designed so that, for at least one of the degrees of freedom, imposed restriction of said degree of freedom can be released when an external effort exerted on the instrument (2; 21) exceeds a predetermined threshold, and
    a computing module (6; 29) for controlling the locking means,
    the guiding device comprises image acquisition means (10; 25), carried by the instrument, for acquiring images of the organ, the computing module being based on at least said images in order to control the locking means; and
    wherein the computing module comprises means for estimating the displacement of the organ relative to the instrument and/or any deformation of the organ, on the basis of images supplied by the image acquisition means, the computing module further comprising monitoring means communicating with the estimating means so as to determine on the basis of the estimated displacement and/or deformation whether locking should be released.

2. The guiding device as claimed in claim 1, wherein the computing module (6; 29) comprises means for storing a position to be reached by the instrument (2; 21) relative to the organ (100; 200), the computing module controlling the locking means, on the basis of the images taken by the image acquisition means (10; 25), so as to impose restriction on at least one of the degrees of freedom of the articulated arm when the instrument is substantially close to said position.

3. The guiding device as claimed in claim 1, wherein the locking means comprise at least one motor (7) arranged on an articulation of the articulated arm (3), the computing module (6) controlling the locking means by modulating an electric current passing through the motor.

4. The guiding device as claimed in claim 1, wherein the locking means comprise at least one brake (30) arranged on an articulation of the articulated arm (27).

5. The guiding device as claimed in claim 1, wherein the locking means are designed so that the predetermined threshold is determined according to external efforts already exerted on the instrument (2; 21) when the locking means (7; 30) impose restriction on the degrees of freedom of the articulated arm (3; 27).

6. The guiding device as claimed in claim 1, comprising communication means (11; 26) for warning that imposed locking has been released.

7. The guiding device as claimed in claim 5, wherein the communication means comprise a display screen (11; 26).

8. The guiding device as claimed in claim 1, comprising means (32) for selecting a first operating mode wherein the locking means are deactivated so that no degree of freedom of the articulated arm (3; 27) is restricted or a second operating mode wherein the locking means are activated so that the degrees of freedom of the articulated arm (3; 27) are restricted.

9. The guiding device as claimed in claim 1, wherein the articulated arm (27) is linked to the proximal end of the instrument (21) by a ball-joint type link (28).

10. The guiding device as claimed in claim 1, comprising weight balancers (9) to balance the articulated arm (3) so that the proximal end (4) of the instrument is held substantially in the center of the duct into which the distal end (1) of the instrument (2) is inserted.

11. A method for controlling the locking means in the device of claim 1, comprising the successive steps of:
acquiring at least one reference image ($I_r$) of the organ (100; 200),
using the image acquisition means (10; 25) to acquire at least a first image ($I_s$) of the organ,
using the computing module (6; 29) to compute a similarity parameter (S) between the reference image and the first image,
using the computing module to compare the similarity parameter with a predetermined similarity threshold ($S_{min}$) representative of the predetermined effort threshold,
using the computing module to control the locking means to release imposed locking if the similarity parameter is below the predetermined similarity threshold.

12. The method for controlling the locking means in the device of claim 1, comprising the successive steps of:
acquiring at least one reference image ($I_r$) of the organ (100; 200),
using the image acquisition means (10; 25) to acquire at least a first image ($I_s$) of the organ,
using the computing module (6; 29) to compute a Euclidean distance parameter ($D_e$) and an angular distance parameter ($D_a$) between the reference image and the first image,
using the computing module to compare the Euclidean distance parameter with a predetermined Euclidean distance threshold ($De_{min}$) and comparing the angular distance parameter with a predetermined angular distance threshold ($Da_{min}$), each of the thresholds being representative of the predetermined effort threshold,
using the computing module to control the locking means to release imposed locking if the Euclidean distance parameter exceeds the predetermined Euclidean distance threshold or if the angular distance parameter exceeds the predetermined angular distance threshold.

13. The method for controlling the locking means in the device of in claim 1, comprising the successive steps of:
acquiring at least one reference image ($I_r$) of the organ (100; 200),
using the image acquisition means (10; 25) to acquire at least a first image ($I_1$) of the organ as soon as the articulated arm is locked,
using the computing module (6; 29) to determine a first position ($T_1$) of the first image relative to the reference image,
using the acquisition means to acquire at least a second image ($I_2$) of the organ,
using the computing module to determine a second position ($T_2$) of the second image relative to the reference image,
computing a Euclidean distance parameter ($D_e$) and an angular distance parameter ($D_a$) between the first position and the second position,
using the computing module to compare the Euclidean distance parameter with a predetermined Euclidean distance threshold ($De_{min}$) and comparing the angular distance parameter with a predetermined angular distance threshold ($Da_{min}$), each of the thresholds being representative of the predetermined effort threshold,
using the computing module to control the locking means to release imposed locking if the Euclidean distance parameter is below the predetermined Euclidean distance threshold or if the angular distance parameter is below the predetermined angular distance threshold.

14. A device for guiding a medical instrument inserted into a natural duct or an artificial duct of a patient in order to bring at least a distal end of the instrument in proximity to an internal organ, the device comprising:
an articulated arm with a plurality of degrees of freedom for moving a proximal end of the instrument;
controlled locking means for restricting the degrees of freedom of the articulated arm, the locking means being designed so that, for at least one of the degrees of freedom, imposed restriction of said degree of freedom can be released when an external effort exerted on the instrument exceeds a predetermined threshold;
a computing module for controlling the locking means; and
image acquisition means, carried by the instrument, for acquiring images of the organ, the computing module being based on at least said images in order to control the locking means and the computing module comprises means for estimating the displacement of the organ relative to the instrument and/or any deformation of the organ on the basis of images supplied by the image acquisition means.

15. The guiding device as claimed in claim 14, wherein the computing module comprises means for storing a position to be reached by the instrument relative to the organ, the computing module controlling the locking means, on the basis of the images taken by the image acquisition means, so as to impose restriction on at least one of the degrees of freedom of the articulated arm when the instrument is substantially close to said position.

16. The guiding device as claimed in claim 14, wherein the locking means comprise at least one motor arranged on an articulation of the articulated arm, the computing module controlling the locking means by modulating an electric current passing through the motor.

17. The guiding device as claimed in claim 14, wherein the locking means comprise at least one brake arranged on an articulation of the articulated arm.

18. The guiding device as claimed in claim 14, wherein the locking means are designed so that the predetermined threshold is determined according to external efforts already exerted on the instrument when the locking means impose restriction on the degrees of freedom of the articulated arm.

19. The guiding device as claimed in claim 14, comprising communication means for warning that imposed locking has been released.

20. The guiding device as claimed in claim 19, wherein the communication means comprise a display screen.

21. The guiding device as claimed in claim 14, comprising means for selecting a first operating mode wherein the locking means are deactivated so that no degree of freedom of the articulated arm is restricted or a second operating mode wherein the locking means are activated so that the degrees of freedom of the articulated arm are restricted.

22. The guiding device as claimed in claim 14, wherein the articulated arm is linked to the proximal end of the instrument by a ball-joint type link.

23. The guiding device as claimed in claim 14, comprising weight balancers to balance the articulated arm so that the proximal end of the instrument is held substantially in the center of the duct into which the distal end of the instrument is inserted.

* * * * *